United States Patent [19]
Woo

[11] 3,943,932
[45] Mar. 16, 1976

[54] ACUPUNCTURE NEEDLES AND HOLDER

[76] Inventor: Yen Kong Woo, 1545 Geary St., Apt. 1, San Francisco, Calif. 94115

[22] Filed: Jan. 17, 1975

[21] Appl. No.: 541,933

[52] U.S. Cl. .................... 128/303.18; 128/329 A
[51] Int. Cl.² .................. A61B 17/40; A61B 17/34
[58] Field of Search ............ 128/329 A, 329 R, 347, 128/303.18

[56] References Cited
UNITED STATES PATENTS

| | | | |
|---|---|---|---|
| 2,919,692 | 1/1960 | Ackermann | 128/329 X |
| 3,410,269 | 11/1968 | Hovick | 128/329 X |
| 3,540,447 | 11/1970 | Howe | 128/347 X |

FOREIGN PATENTS OR APPLICATIONS

| | | | |
|---|---|---|---|
| 55,511 | 8/1935 | Norway | 128/347 |

*Primary Examiner*—Channing L. Pace

[57] ABSTRACT

A plurality of relatively adjustable acupuncture needles including a holder in which any selected needle may be removably mounted for operative use.

8 Claims, 13 Drawing Figures

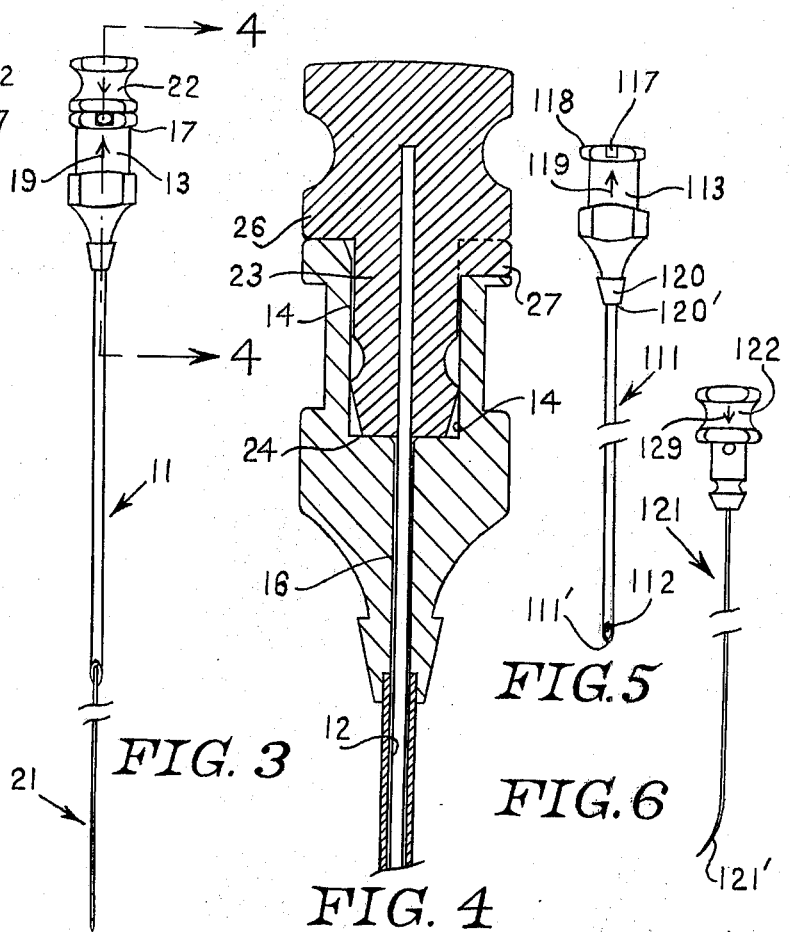

ACUPUNCTURE NEEDLES AND HOLDER

In relatively recent years the art of acupuncture has received an increasing degree of attention and many new devices have been developed for treating patients by employing acupuncture. Some of these devices include electrical instruments for locating an area of a patient's body where the nerve is out of balance or otherwise adversely affected and, hence, subject to stimulus by means of acupuncture. Reference in this connection is made to U.S. Pat. No. 3,626,202 of Dec. 7, 1971 and to the United States and foreign patents therein cited. The present invention is directed to acupuncture needles per se and to an acupuncture needle holder which may be facilely assembled and connected together for acupunctual uses either with or without augmentation of electrical circuitry.

A primary object of my invention is to provide acupuncture needles of relative adjustability as to length with respect to one another, in combination with a holder which per se is an acupuncture needle and in which any of the needles may be removably mounted.

Another important object of my present invention is to provide acupuncture needles and holder of the indicated nature which is additionally characterized by affording relatively adjustable needles of indeterminate length which are more serviceable, more effective and less expensive to manufacture and maintain.

A still further object of the invention is to provide acupuncture needles and holder of the aforementioned character which, in addition to the foregoing features, are break-proof thus affording increased safety in use by reducing to a minimum the likelihood of injury to the human body.

Another important object of my invention is to provide acupuncture needles and holder of the indicated nature which enables simultaneous stimuli of a plurality of weakened spots of the nerves at locations in the body remote from one another.

A still further object of the invention is to provide acupuncture needles and holder which is additionally characterized by the inclusion in a set thereof of a specially constructed needle enabling transmission of electrically induced waves in desired directions using appreciably low voltage direct current to prevent any damage to patients.

Other objects of my invention, together with some of the advantageous features thereof, will appear from the following description of certain embodiments thereof illustrated in the accompanying drawings which exemplify the best mode of constructing the invention and the manner of using the same. It is to be understood that the appended claims are intended to cover not only the embodiments illustrated but also variations thereof within the scope and purview of my invention.

Referring to the drawings:

FIG. 1 is an elevational view of an acupuncture needle holder which is common to all needle mountings of my present invention, with indicator arrow delineated thereon.

FIG. 2 is a fragmentary or broken elevational view of an elongated type of acupuncture needle of my invention removably mountable in the holder of FIG. 1.

FIG. 3 is an elevational view of the combined holder and the elongated needle of FIG. 2 mounted therein for operative use; this view showing the standard or common holder of a different length than the holder shown in FIG. 1.

FIG. 4 is an enlarged cross-sectional view of the head of the common holder latched to the head of the elongated acupuncture needle illustrated in FIG. 2; this view being taken on the line 4—4 of FIG. 3.

FIG. 5 is a broken elevational view of the standard or common acupuncture needle or shield, this view being similar to FIG. 1.

FIG. 6 is a broken elevational view of a modified acupuncture needle containing a fixed terminal bend.

FIG. 7 is a perspective view of the bent end needle of FIG. 6 as well as a perspective view of the acupuncture needle holder of FIG. 5 in juxtaposition and illustrating the manner of holding these two elements for introducing the bent end needle into the holder.

FIG. 8 is an elevational view of both the bent end needle of FIG. 6 and of the needle holder of FIG. 5 in partially assembled relation; the dotted line indicating the position of a portion of the bent end needle in the holder.

FIG. 9 is an enlarged fragmentary view of the bent end needle within and extending beyond the pointed tip of the holder; this view showing the bent end of the inner needle pointing to the left.

FIG. 10 is a view similar to FIG. 9 but with the bent end of the inner needle pointing to the right.

FIG. 11 is a fragmentary elevational view of the combined needle holder and inner needle with applied dried goat's intestines, the dotted lines indicating the inner needle.

FIG. 12 is a fragmentary elevational view of the inner needle which moves the goat's intestines out of the holder in which it is carried and into a treated muscle of the body.

FIG. 13 is a view of the combined showings of FIGS. 11 and 12 with the applied dried goat's intestines on the inner needle after being moved out of the holder.

In accordance with my invention, I provide a primary acupuncture needle which is generally designated by the reference numeral 11 and fashioned with a chamfered or pointed tip 11' to facilitate insertion and movement of the needle into and beyond the skin of a patient. The needle 11 is so formed as to define a coextensive passage 12 therethrough and being tubular affords not only an outer acupuncture needle per se but primarily a shield and holder for any selected one of a plurality of different acupuncture needles in one or more sets thereof as hereinafter described. The holder 11 carries an integral head 13 having a flat-bottomed cavity 14 therein, see FIG. 4, which communicates with a centrally disposed bore 16 in the head which, in turn, is in communication with the central passage 12 of acupuncture needle holder 11. I conveniently provide a notch 17 in the rim 18 of the top of the head 13 of holder 11 and delineate thereon or die-cut therein an indicator arrow 19 for a purpose hereinafter explained. The head 13 is tapered as shown in FIG. 1 to a neck 20 having an apertured annular base 20' through which the upper end of the holder 11 extends.

As particularly illustrated in FIGS. 2 and 3 of the annexed drawings, my improved acupuncture needles and holder include an inner elongated stainless steel acupuncture needle 21 of indeterminate length but of greater length and of less guage or less cross-section than the length and cross-section of the primary acupuncture or outer needle or holder 11. Integrally cast with inner needle 21 is a stemmed head 22 for convenient grasping thereof and for enabling reciprocation of the inner needle 21 with respect to the holder 11 after both acupuncture needles 11 and 21 have been introduced into the human body. The holder 11 initially is introduced below the surface of the skin into the muscle for a predetermined distance which is fixed by the length of the holder selected with the base 20' of the head 13 thereof abutting the outer surface of the skin. In this position of the outer needle or holder 11, it remains set and stationary under a pain-sensitive layer. Thereafter, the inner acupuncture needle 21 is introduced into the muscle through the passage 12 of the holder or shield 11 and such selected inner needle 21 is then reciprocated back and forth or up and down within the pierced muscle, either electrically by means of a battery-operated machine using not more than 9 volts direct current, and finally brought to rest at a nerve spot which is to be treated; such movement of the inner acupuncture needle causing little or no pain whatsoever inasmuch as it is moved in muscle areas only and does not rub or brush against any sensitive layer of the skin by virtue of the protective shield of the outer tubular holder 11. Any likelihood of breaking the relatively thin inner long acupuncture needles 21 is reduced to a minimum by reason of the outer protective holder 11 and damage to the body of the patient is virtually eliminated. It is to be observed that the stem portion 23 of the head 22 of the needle 21 is formed with a flat base 24 which seats on the flat bottom of cavity 14 when the two needles are brought together and latched in relation to one another at the at rest position of the inner needle 21. To this end, the flange 26 of the head 22 is formed with a depending portion 27 which removably fits the notch 17 in the run 18 of the outer needle or holder 11. In the embodiment illustrated in FIGS. 1 to 4 inclusive the cavity 14 is formed to a cylindrical configuration to rotatably seat and reciprocally receive the cylindrical stem 23 of the head 22 of an inner acupuncture needle 21. This shape is not critical however, and any other suitable means of detachably connecting heads 13 and 22 can be employed as desired.

A modified embodiment of my present invention and its best mode of construction and manner of using the same is illustrated in FIGS. 5 to 10 of the accompanying drawings. In this modification, an outer or primary acupuncture needle 111 having a chamfered pointed tip 111' and defining a central passage 112 therein is provided as a protective outer shield, as shown in the broken elevational view of FIG. 5. This holder 111 is cast from stainless steel with an integral head 113 thereon of the same form and shape as the head 13 of the embodiment of my invention shown in FIG. 1. I also provide in this modification a specially constructed inner acupuncture needle 121 of indeterminate length but provided with a bent outer or terminal end 121'. It is, of course, to be understood that the guage of such modified acupuncture needle 121 and the entire length of the needle is resilient to some extent but of sufficient rigidity as to enable the needle to be moved into the muscle with the only deviation from a straight line occuring at its outer bent end 121'. It is also to be observed that the degree of curvature of such outer extremity of the needle 121 is not critical; its purpose being primarily for giving direction to an electrical wave of light voltage, as above stated, whenever the acupuncture needle 121 is actuated by an electrical circuit which, it is to be further observed affords some beneficial heat to the needle.

In FIGS. 7 and 8, I have illustrated the method of combining the outer and inner acupuncture needles 111 and 121, respectively, or the method of threading the inner needle with its bent end 121' through the passages 112 of the shield or outer needle 111. Using one hand to hold the bent end needle 121 in a position at an angle to the vertical, and using the other hand to hold the shield or holder 111 at a reverse inclination to the vertical but in close proximity to the outer tip of the inner needle, the bent end 121' of needle 121 is fed into the cavity of the head 113 and through the bore of such head and thence into the aligned central passage 112 of the holder. The two needles are brought into axial alignment with one another, as shown in FIG. 8, with the inner needle extending partly through such inner passage 112, as indicated by the dotted line showing of FIG. 8. The bent end 121' of needle 121 is then further extended to a position exterior of the holder 111 with the bent end 121' projected and directed to the left as shown in FIG. 9. Should it be desired to project the bent end 121' of inner needle 121 to the right, as illustrated in FIG. 10, it is only necessary before inserting such needle into the passage 112 of the holder 111, to turn the bent end in a right direction and proceed as before to project the directional bent end 121' to the right. In order to place the bent end 121' in any selected angular direction with respect to the outer end of the needle 111 within a 360° angle, it is only necessary first to place the bent end in a selected angle with respect to the head 113 of the holder 111 and introduce the same through the passage 112 thereof so as to project such bent end 121' in the desired selected angular direction, which can readily be adjusted by first unlatching the head 122 of the inner needle from the head 113 of the outer needle 111. Thus, as is clear from the foregoing, electrical waves from an electrical circuit energized by as low as a 9 volt direct current source, such as a storage battery, so as not to be injurious to the patient, can be directed within 360° to any selected area of the body as determined by the attending surgeon.

As illustrated, the modified embodiment of FIGS. 5-10 inclusive, comprises needle heads in all respects similar to the heads 13 and 22 of the outer needle or holder 11 and of the elongated needle 21, respectively with an indicator arrow 129 on the head 122 of the bent end needle 121 for matching up or aligning with the indicator arrow 119 of the head 113 of the shield or holder 111 when joining said needles together. Similar latching elements are carried on the heads 113 and 122 of the shield or protector acupuncture needle 111 and the bent end acupuncture needle 121 for detachably connecting such two needles together.

A fragmentary showing of still another modified embodiment of my present invention appears on FIGS. 11, 12 and 13 of the annexed drawings. In this further modification, similar needle heads as well as similar interlocking elements, all not shown in these views, as are used in the embodiments of FIGS. 1–3, inclusive, and of FIGS. 5–10 inclusive. Such needle heads and such interlocking elements, in other words, are common to all embodiments and are clearly shown in the enlarged view of FIG. 4. My invention in the modification of FIGS. 11–13, inclusive, comprises all of the foregoing elements and the addition of a quantity or mass of dried goat's intestines disposed within the tubular holder 211 and extending along the wall of passage 212 thereof a distance of approximately ½ inch; such mass extending either from the top of the needle or from the pointed tip 211' thereof as shown by the dotted lines in FIG. 11 and designated by the reference numeral 226. When the inner needle 221 of this modification is threaded through the passage 212, the outer end of such inner needle picks up the mass of dried goat's intestines and injects it, as indicated by the reference numeral 227, see FIG. 13, into the human muscle. During the decomposition of the dried intestines of a goat, which is a natural phenomena, the movement of the muscle will homogeneously and simultaneously stimulate the nearby or adjacent nervous system, i.e., the weakened part thereof so that it will resume its normal function.

I claim:

1. Acupuncture needles and holder comprising an outer tubular shield having a central passage therein of uniform cross-section coextensive with its length, a chamfered tip on the terminal end of said shield, and an inner elongated acupuncture needle mounted for reciprocation within said central passage for movement relative to said outer tubular shield beyond said chamfered tip thereof.

2. Acupuncture needles and holder as set forth in claim 1, wherein said outer tubular shield includes a head having a cavity therein and wherein said elongated acupuncture needle includes a stemmed head removably mounted in said cavity.

3. Acupuncture needles and holder as set forth in claim 1 wherein said tubular shield constitutes an acupuncture inner elongated acupuncture needle.

4. Acupuncture needles and holder as set forth in claim 2, and interlocking elements on said head of said outer tubular shield and on said head of said inner elongated acupuncture needle for detachably connecting the same.

5. Acupuncture needles and holder as set forth in claim 1 wherein said inner acupuncture needle has a bent terminal end extendable beyond said chamfered tip on said outer tubular shield for directing low voltage current applied thereto in an elected direction.

6. Acupuncture needles and holder as set forth in claim 1, and a mass of dried goat's intestines on a portion of said outer tubular shield for transfer to said inner elongated acupuncture needle and thereby to a muscle of the human body by passing said inner acupuncture needle through the passage of said outer tubular shield.

7. Acupuncture needles and holder as set forth in claim 5 and capable of transmitting waves of applied electrical low voltage direct current energy in the order of 9 volts, wherein said inner needle with said bent terminal end is movably mounted within said outer tubular shield and latchable in any selected one of a plurality of positions within 360° to cause said waves of applied electrical energy to move in a selected direction.

8. Acupuncture needles and holder as set forth in claim 1 wherein the central passage of said outer tubular shield is of sufficient diameter to pass a solid.

* * * * *